United States Patent
Liang et al.

(10) Patent No.: US 8,198,320 B2
(45) Date of Patent: Jun. 12, 2012

(54) HYPOGLYCEMIC ACTIVITY OF OSTHOLE

(75) Inventors: Yu-Chih Liang, Taipei (TW); Der-Zen Liu, Taipei (TW); Ling-Fang Hung, Taipei (TW); Pei-Jung Lin, Taipei (TW); Nai-Qi Chen, Taipei (TW); Yu-Chien Chen, Taipei (TW)

(73) Assignee: Taipei Medical University, Taipei (TW)

( * ) Notice: Subject to any disclaimer, the term of this patent is extended or adjusted under 35 U.S.C. 154(b) by 552 days.

(21) Appl. No.: 12/347,429

(22) Filed: Dec. 31, 2008

(65) Prior Publication Data

US 2010/0168224 A1    Jul. 1, 2010

(51) Int. Cl.
*A61K 31/35* (2006.01)
*A61K 31/155* (2006.01)
*A61K 36/00* (2006.01)

(52) U.S. Cl. ......... 514/457; 514/635; 514/866; 424/725

(58) Field of Classification Search ................. 514/457, 514/635; 424/725
See application file for complete search history.

(56) References Cited

U.S. PATENT DOCUMENTS 3,174,901 A * 3/1965 Sterne ........................... 514/635

FOREIGN PATENT DOCUMENTS

| CN | 101095669 A | 1/2008 |
| TW | 564177 B | 12/2003 |

OTHER PUBLICATIONS

Ojewole, "Hypoglycaemic effect of Clausena anisata (Wild) Hook methanolic root extract in rats", Journal of Ethnopharmacology, vol. 81, No. 2, pp. 231-237 (2002).*

Liang et al., "Osthole, a potential antidiabetic agent, alleviates hyperglycemia in db/db mice", Chemico-Biological Interactions, vol. 181, No. 3, pp. 309-315 (2009).*

Wei, Y. et al., "Preparative isolation of osthole and xanthotoxol from Common Cnidium Fruit using stepwise elution by high-speed counter-current chromatography (HSCCC)." J. Chromatogr. A. 2004, 1033(2):373-377.

Chiou, W. F. et al., "Vasorelaxing effect of coumarins from *Cnidium monnieri* on rabbit corpus cavernosum." Planta. Med. 2001, 67(3):282-284.

Guh, J. H. et al., "Antiproliferative effect in rat vascular smooth muscle cells by osthole, isolated from Angelica pubescens." Eur. J. Pharmacol. 1996, 298(2):191-197.

Wu, S. N., "Inhibitory effect of the plant-extract osthole on L-type calcium current in NG108-15 neuronal cells." Biochem. Pharmacol. 2002, 63(2):199-206.

Matsuda, H. et al., "Anti-allergic effects of *Cnidii monnieri* fructus (dried fruits of *Cnidium monnieri*) and its major component, osthole." Biol. Pharm. Bull. 2002, 25(6):809-812.

Okamoto, T. et al., "Osthole prevents anti-Fas antibody-induced hepatitis in mice by affecting the caspase-3-mediated apoptotic pathway." Biochem. Pharmacol. 2003, 65(4):677-681.

Chou, S. Y., "Antitumor effects of Osthole from *Cnidium monnieri*: an in vitro and in vivo study." Phytother. Res. 2007, 21(3):226-230.

Ogawa, H. et al., "Effects of osthol on blood pressure and lipid metabolism in stroke-prone spontaneously hypertensive rats." J. Ethnopharmacol. 2007, 112(1):26-31.

Sun, F. et al., "Inhibitory effect of osthole on alcohol-induced fatty liver in mice." Dig. Liver Dis. available online on Mar. 11, 2008.

Zhang, Y. et al., "Therapeutic effect of osthole on hyperlipidemic fatty liver in rats." Acta Pharmacol. Sin. 2007, 28 (3):398-403.

Kuo, P. L. et al., "Osthole-mediated cell differentiation through bone morphogenetic protein-2/p38 and extracellular signal-regulated kinase 1/2 pathway in human osteoblast cells." J. Pharmacol. Exp. Ther. 2005, 314(3):1290-1299.

Zhang, Q. et al., "Coumarins from *Cnidium monnieri* and their antiosteoporotic activity." Planta. Med. 2007, 73 (1):13-19.

Li, X. X. et al., "Effects of osthole on postmenopausal osteoporosis using ovariectomized rats; comparison to the effects of estradiol." Biol. Pharm. Bull. 2002, 25(6):738-742.

* cited by examiner

*Primary Examiner* — Kevin E Weddington
(74) *Attorney, Agent, or Firm* — McDonnell Boehnen Hulbert & Berghoff LLP

(57) ABSTRACT

The present invention relates to a method for controlling blood glucose level and a method for the prophylaxis or treatment of diabetes mellitus and/or its complications. The present invention further relates to an anti-diabetic formulation for controlling blood glucose level and/or for the prophylaxis or treatment of diabetes mellitus and/or its complications.

10 Claims, 2 Drawing Sheets

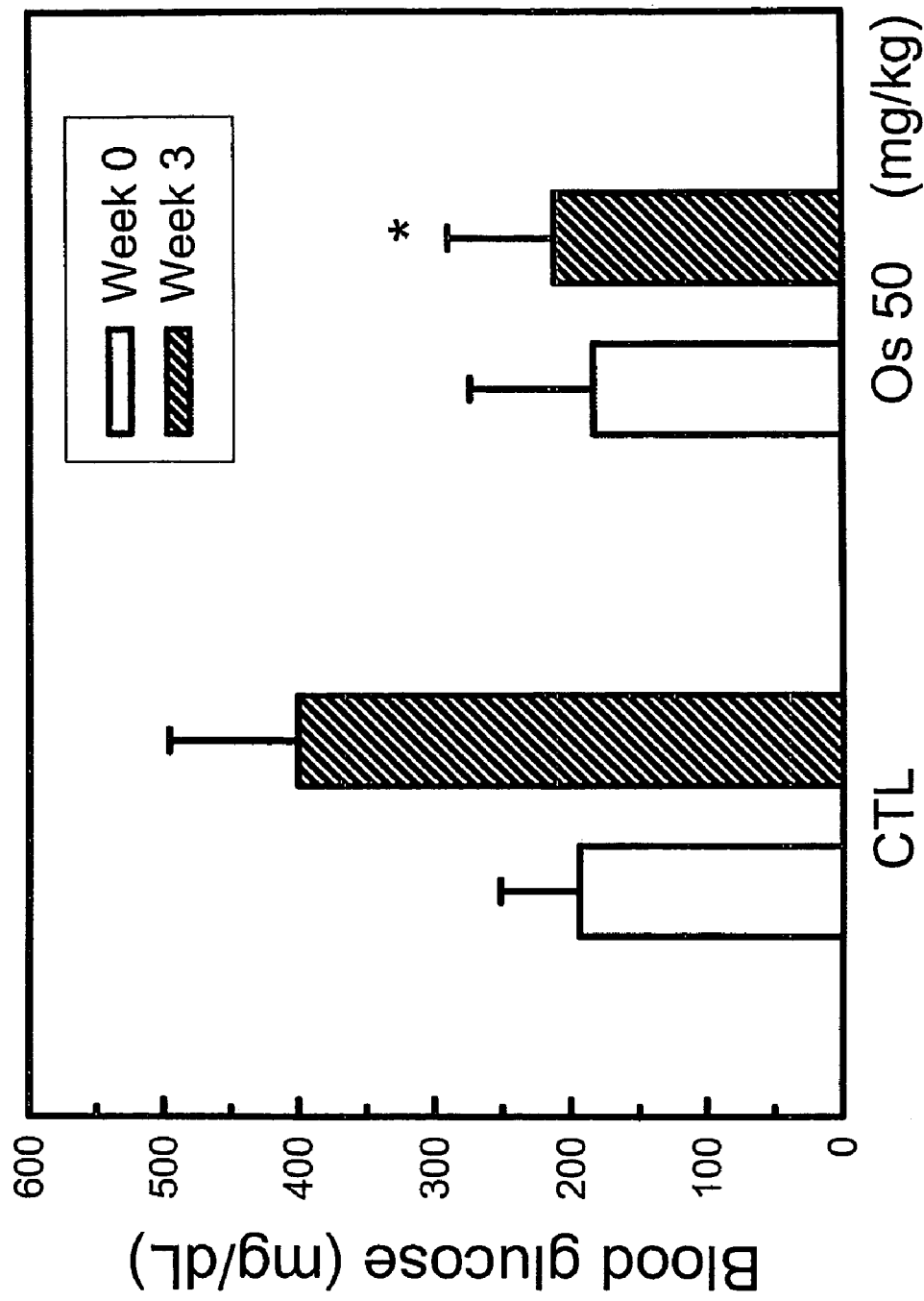

HYPOGLYCEMIC ACTIVITY OF OSTHOLE

FIELD OF THE INVENTION

The present invention relates to a method for controlling blood glucose level and a method for the prophylaxis or treatment of diabetes mellitus and/or its complications. The present invention further relates to an anti-diabetic formulation for controlling blood glucose level and/or for the prophylaxis or treatment of diabetes mellitus and/or its complications.

BACKGROUND OF THE INVENTION

The following discussion is to facilitate the understanding of the invention, but is not intended as reference to prior art.

Diabetes mellitus, often referred to simply as diabetes, is a syndrome of disordered metabolism, usually due to a combination of hereditary and environmental causes, resulting in abnormally high blood glucose level (hyperglycemia). Blood glucose level is controlled by a complex interaction of multiple chemicals and hormones in the body, including the hormone insulin made in the beta cells of the pancreas. Diabetes mellitus refers to the group of diseases that lead to high blood glucose level due to defects in either insulin secretion (Type I diabetes) or insulin action (Type II diabetes). Both Type I and Type II diabetes lead to hyperglycaemia, which largely causes the acute signs of diabetes: excessive urine production, resulting compensatory thirst and increased fluid intake, blurred vision, unexplained weight loss, lethargy, and changes in energy metabolism.

Hyperglycemia may cause long-term microvascular and macrovascular complications, such as nephropathy, neuropathy, retinopathy, and peripheral vascular disease. In addition, diabetes is a comorbid disease that frequently compounds hyperlipidemia, atherosclerosis and hypertension. Hyperlipidemia is a primary risk factor for cardiovascular disease due to atherosclerosis. The long-term complications of diabetes usually are decreased life expectancy, neuropathy, and an increased rate of blindness, kidney disease and heart disease in comparison to nondiabetics.

Diabetes may be controlled with insulin and in some cases through careful diet. However, the blood glucose level will still fluctuate (sometimes dramatically) in patients undergoing insulin or diet therapy. Furthermore, in cases where the diabetes is severe, patients find it necessary to constantly monitor their glucose level to prevent associated illnesses. Diabetic patients are forced to inject insulin which ultimately leads to bruising in certain areas. Furthermore, additional medical complications often arise from diabetes such as arteriosclerosis, hyperlipidemia, retinal damage, neurological damage, fatigue and weakness.

Therefore, there is a need for a safe and effective treatment of diabetes with minimal side effects and/or without the invasive procedures, such as injections.

She chuang zi, also known as Cnidium fruit, fructus cnidii she li, she mi, Taiwan chuan xiong, jia yuan sui and ye hu lo fu zi, is the dried fruit of Cnidium monnieri (L.) Cuss. It has been long used in China as a herb medicine for the treatment of impotence, dampness, infertility, lumbar pain, liking parasites, eczema or vaginal itchiness, itchy skin, trichomoniasis, rectal prolapse, hemorrhoid, and the like. In terms of properties, Cnidium fruit is acrid, bitter and warm. Cnidium monnieri (L.) Cuss. is mainly found in Hebei, Shandong, Zejiang, Jiangsu, Sichuan and Taiwan. The known active ingredients of Cnidium fruit include L-pinene, L-camphene, bornyl isovalarate, isoborneol, osthole, cnidimine (eduotin), cnidiadin, isopimpinelline, xanthotoxol, etc.

Osthole is a coumarin compound, named 7-methoxy-8-isopentenylcoumarin or 7-methoxy-8-(3-methyl-2-butenyl)-2H-1-benzopyran-2-one, which has the following chemical structure:

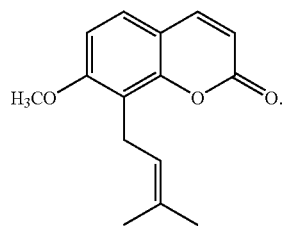

TW564177B discloses a method for the extraction of osthole from Cnidium fruit, the anti-Tricholmonase vaginalis preparation containing osthole as the main ingredient, and the method of determination of the anti-Trichomonas vaginalis activity of the osthole-containing preparation. Wei, Y., et al., disclose preparative isolation of osthole and xanthotoxol from Common Cnidium Fruit using stepwise elution by high-speed counter-current chromatography (HSCCC) (see J. Chromatogr. A. 2004, 1033(2):373-377). CN101095669A discloses osthole phospholipid complexes, the preparation method thereof and the application, to increase the solubility of osthole.

Recent studies show that osthole has effects on the cardiovascular system, the neural system, the immune system and the metabolism of lipid and bone, such as vascular dilating (see Chiou, W. F., et al., "Vasorelaxing effect of coumarins from Cnidium monnieri on rabbit corpus cavernosum." Planta. Med. 2001, 67(3):282-284), inhibiting the proliferation of vascular smooth muscle cells (see Guh, J. H., et al., "Antiproliferative effect in rat vascular smooth muscle cells by osthole, isolated from Angelica pubescens." Eur. J. Pharmacol. 1996, 298(2):191-197), inhibiting the ionic currents in neuronal cells (see Wu, S. N., "Inhibitory effect of the plant-extract osthole on L-type calcium current in NG108-15 neuronal cells." Biochem. Pharmacol. 2002, 63(2):199-206), anti-allergy (see Matsuda, H., et al., "Anti-allergic effects of cnidii monnieri fructus (dried fruits of Cnidium monnieri) and its major component, osthole." Biol. Pharm. Bull. 2002, 25(6):809-812), preventing hepatitis (see Okamoto, T., et al., "Osthole prevents anti-Fas antibody-induced hepatitis in mice by affecting the caspase-3-mediated apoptotic pathway." Biochem. Pharmacol. 2003, 65(4):677-681), inhibiting the growth of tumor cells (see Chou, S. Y., "Antitumor effects of Osthole from Cnidium monnieri: an in vitro and in vivo study." Phytother. Res. 2007, 21(3):226-230), reducing blood lipid and lowering blood pressure (see Ogawa, H., et al., "Effects of osthol on blood pressure and lipid metabolism in stroke-prone spontaneously hypertensive rats." J. Ethnopharmacol. 2007, 112(1):26-31), inhibiting alcohol or fatty milk-induced fatty liver (see Sun, F., et al., "Inhibitory effect of osthole on alcohol-induced fatty liver in mice." Dig. Liver Dis. available online on 11 Mar. 2008; and Zhang, Y., et al., "Therapeutic effect of osthole on hyperlipidemic fatty liver in rats." Acta Pharmacol. Sin. 2007, 28(3):398-403), and suppressing osteoporosis (see Kuo, P. L., et al., "Osthole-mediated cell differentiation through bone morphogenetic protein-2/p38 and extracellular signal-regulated kinase ½ pathway in human osteoblast cells." J. Pharmacol. Exp. Ther. 2005, 314 (3):1290-1299; Zhang, Q., et al., "Coumarins from Cnidium monnieri and their antiosteoporotic activity." *Planta. Med.* 2007, 73(1):13-19; and Li, X. X., et al., "Effects of osthole on postmenopausal osteoporosis using ovariectomized rats; comparison to the effects of estradiol." *Biol. Pharm. Bull.* 2002, 25(6):738-742). There is no report of the effect of osthole on the regulation of blood glucose level.

SUMMARY OF THE INVENTION

One of the purposes of the present invention is to provide a method for controlling blood glucose level comprising administering a therapeutically effective amount of osthole or a pharmaceutically acceptable derivative thereof to a subject in need thereof, thereby reducing the blood glucose level in the subject. In particular, the blood glucose level is elevated due to diabetes mellitus.

Another purpose of the present invention is to provide a method for the prophylaxis or treatment of diabetes mellitus and/or its complications comprising administering a therapeutically effective amount of osthole or a pharmaceutically acceptable derivative thereof to a subject in need thereof.

The present invention also relates to an anti-diabetic formulation comprising a therapeutically effective amount of osthole or a pharmaceutically acceptable derivative thereof and a pharmaceutically acceptable carrier or excipient.

The present invention is described in detail in the following sections. Other characteristics, purposes and advantages of the present invention can be easily found in the detailed descriptions and claims.

BRIEF DESCRIPTION OF THE DRAWINGS

FIG. 2 shows the blood glucose level of db/db diabetic mice before and after oral administration of osthole and PBS.

DETAILED DESCRIPTION OF THE INVENTION

Figure 1:
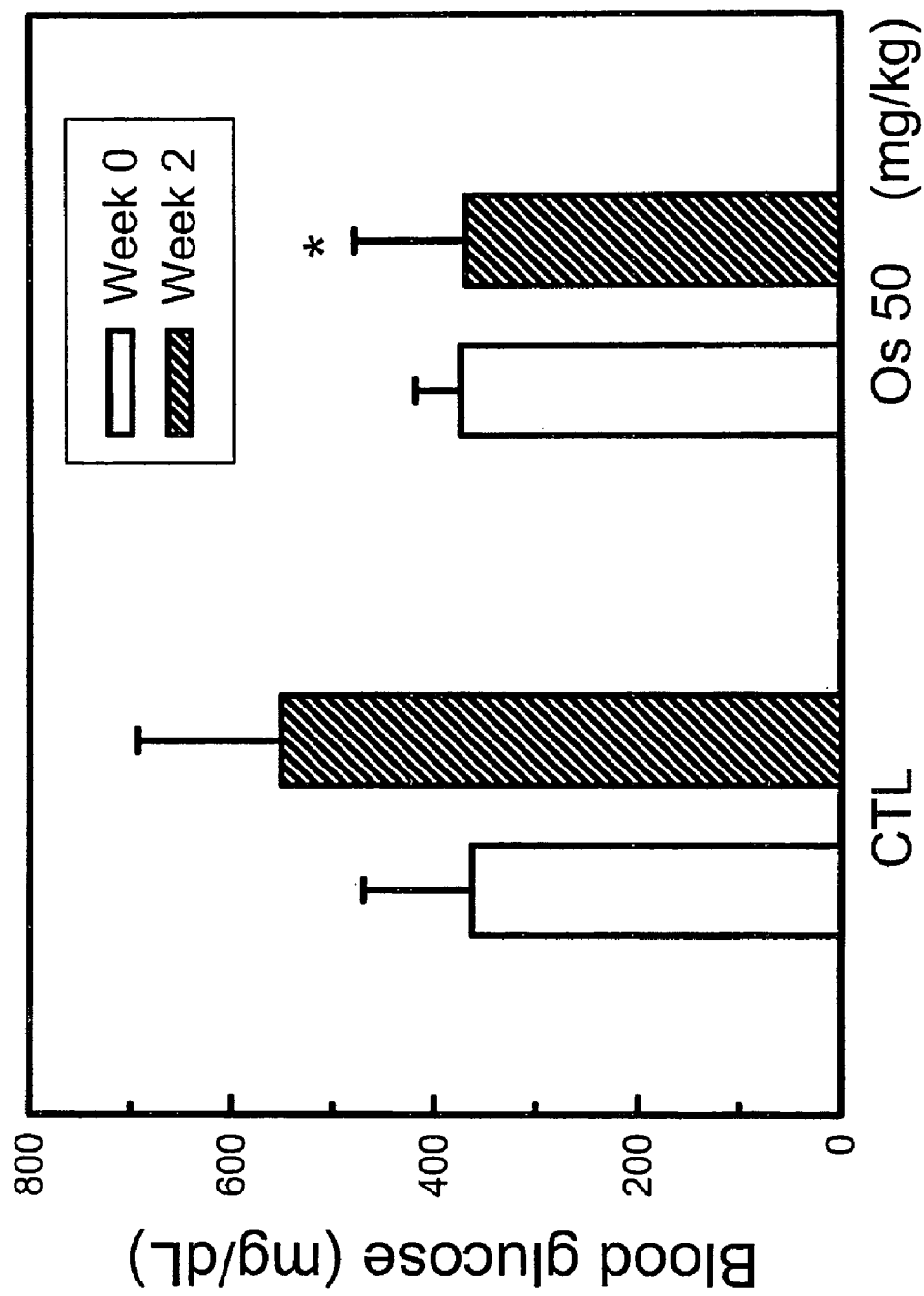
FIG. 1 shows the blood glucose level of db/db diabetic mice before and after intraperitoneal administration of osthole and DMSO.

Unless otherwise defined herein, scientific and technical terms used in connection with the present invention shall have the meaning commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings:

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "osthole" as used herein denotes a compound named 7-methoxy-8-isopentenylcoumarin or 7-methoxy-8-(3-methyl-2-butenyl)-2H-1-benzopyran-2-one.

The term "pharmaceutically acceptable derivatives" as used herein denotes a compound that is modified from osthole but has the properties and efficacy as the same as or better than osthole. Preferably, the pharmaceutically acceptable derivative is pharmaceutically acceptable salt, solvate or prodrug of osthole. For example, the compound may be conjugated with other materials to increase its solubility.

The term "therapeutically effective amount" as used herein refers to an amount effective at dosages and for periods of time necessary to achieve the desired result. The therapeutically effective amount of an agent may vary with factors such as the disease state, physical conditions, age, sex, species and weight of the subject. Dosage regimens may be adjusted to induce the optimum therapeutic response. For example, several divided doses may be administered daily or the dose may be proportionally reduced as indicated by the exigencies of the therapeutic situation.

The term "prophylaxis" is art-recognized, and when used in relation to a condition includes administering, prior to onset of the condition, an agent to reduce the frequency or severity of or delays the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulation or food product. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Unless otherwise required by context, singular terms shall include the plural and plural terms shall include the singular.

Therapeutic Use

The present invention relates to a surprising discovery that osthole or a pharmaceutically acceptable derivative thereof has hypoglycemic activity and therefore can be used to control blood glucose level in a subject and to treat diabetes mellitus and/or its complications.

In one preferred embodiment, the blood glucose level is elevated due to diabetes mellitus. In one embodiment, the diabetes mellitus is Type I diabetes. In another embodiment, the diabetes mellitus is Type II diabetes. In certain embodiments, the complications of diabetes is selected from the group consisting of hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity.

According to the method of the present invention, osthole or a pharmaceutically acceptable derivative thereof can be obtained by chemically synthesized or extracted from osthole-containing plants. The methods of synthesizing or isolating osthole or a pharmaceutically acceptable derivative thereof are known in the art (such as TW564177B and CN1089497A; the disclosure of the applications are incorporated herein by reference in its entirety). In one embodiment of the invention, osthole or a pharmaceutically acceptable derivative thereof is obtained from *Cnidium* plant. Preferably, osthole or a pharmaceutically acceptable derivative thereof is obtained from *Cnidium monnieri* (L.) Cuss. More preferable, osthole or a pharmaceutically acceptable derivative thereof is obtained from *Cnidium* fruit. In another embodiment of the invention, the amount of osthole in the extract of the osthole-containing plants is higher than 10%, more preferably higher than 50%, most preferably higher than 95%.

According to the method of the present invention, the therapeutically effective amount is about 10 to about 200 mg/kg/day, preferably about 40 to about 100 mg/kg/day, most preferably about 50 mg/kg/day.

According to the method of the present invention, osthole or the pharmaceutically acceptable derivative thereof can be administered locally or systemically by any method known in the art, including, but not limited to, intramuscular, intradermal, intravenous, subcutaneous, intraperitoneal, intranasal, oral or other mucosal routes. The appropriate route, formulation and immunization schedule can be determined by those skilled in the art. Osthole or the pharmaceutically acceptable derivative thereof can be administered with a suitable, non-toxic pharmaceutical carrier or excipient, or can be in the form of a liquid solution, a suspension, an emulsion, a syrup, a tablet, a pill, a capsule, a sustained release formulation, a powder, a granule, an ampoule, an injection, an infusion or a combination thereof or a dietary product.

According to the method of the present invention, osthole or the pharmaceutically acceptable derivative thereof can be administered in combination with a second agent effective for controlling blood glucose level, thereby reducing the blood glucose level in a subject. Many agents are known in the art to be effective for controlling blood glucose level. Examples of such agents include, but are not limited to, sulfonylureas (such as glipizide, glimepiride, and glyburide), biguanides (such as metformin), α-glucosidase inhibitors (such as acarbose and miglitol), meglitinides (such as nateglinide and repaglinide), thiazolidinediones (such as pioglitazone and rosiglitazone), amylinomimetic (such as pramlintide), GLP-1 analog (such as exnatide) and DPP4 inhibitors (such as sitagliptin and vildagliptin) (see Langley, A. K., et al., "Dipeptidyl peptidase IV inhibitors and the incretin system in type 2 diabetes mellitus." *Pharmacotherapy* 2007, 27(8):1163-1180; and Doupis, J. and Veves, A., "DPP4 inhibitors: a new approach in diabetes treatment." Adv. Ther. 2008, 25(7):627-643).

According to the method of the present invention, osthole or the pharmaceutically acceptable derivative thereof can be administered in combination with a second agent effective for the prophylaxis or treatment of diabetes mellitus. Many agents are known in the art to be effective for the prophylaxis or treatment of diabetes mellitus. Examples of such agents include, but are not limited to, sulfonylureas (such as glipizide, glimepiride, and glyburide), biguanides (such as metformin), α-glucosidase inhibitors (such as acarbose and miglitol), meglitinides (such as nateglinide and repaglinide), thiazolidinediones (such as pioglitazone and rosiglitazone), amylinomimetic (such as pramlintide), GLP-1 analog (such as exnatide) and DPP4 inhibitors (such as sitagliptin and vildagliptin) (see Langley, A. K., et al., "Dipeptidyl peptidase IV inhibitors and the incretin system in type 2 diabetes mellitus." *Pharmacotherapy* 2007, 27(8):1163-1180; and Doupis, J. and Veves, A., "DPP4 inhibitors: a new approach in diabetes treatment." Adv. Ther. 2008, 25(7):627-643).

Formulations

The present invention also provides an anti-diabetic formulation comprising a therapeutically effective amount of osthole or a pharmaceutically acceptable derivative thereof and a pharmaceutically acceptable carrier or excipient. The therapeutically effective amount is defined and described in the above sections. Persons skilled in the art should have no difficulty choosing the suitable routes and the dosages for treatment.

In one preferred embodiment, the formulation of the invention is a medicament. According to the present invention, the medicament can be formulated in various ways, according to the corresponding route of administration, such as liquid solution, a suspension, an emulsion, a syrup, a tablet, a pill, a capsule, a sustained release formulation, a powder, a granule, an ampoule, an injection, an infusion, a kit or a combination thereof. The medicament can also contain a carrier or excipient, many of which are known to one of ordinary skill in the art, see paragraph [0024] for example.

In one preferred embodiment, the formulation of the invention is a dietary product. According to the present invention, the dietary product can be a food substance, a health food, a food supplement, a medical food, a liquid, a beverage, a feed or a mixture thereof. The dietary product can also contain a carrier or excipient, many of which are known to one of ordinary skill in the art, see paragraph [0024] for example.

According to the present invention, anti-diabetic formulation can be used in combination or further comprise an agent or dietary product effective for the prophylaxis or treatment of diabetes mellitus.

The following examples are provided to aid those skilled in the art in practicing the present invention.

EXAMPLES

Example 1

Effect of Intraperitoneal Administration of Osthole to Diabetic Mice

Six male db/db diabetic mice (6 to 11 week-old, purchased from National Laboratory Animal Center (Taipei, Taiwan)) were fasted for over 8 hours and venous blood was collected for the measurement of blood glucose level. The mice were divided into two groups (control group and experimental group) on the basis of their blood glucose level and body weight. The mice in the control group were given the solvent DMSO by means of intraperitoneal administration. The mice in the experimental group were given osthole (50 mg/kg body weight) (purchased from Hangzhou Gosun Biotechnologies Co., Zhejiang, China) by means of intraperitoneal administration. The solvent and osthole were administered once daily, five days a week for two weeks. The mice were then fasted for about 16 hours before being sacrificed and blood samples were collected for the measurement of blood glucose levels. The results of blood glucose level measurement are shown in FIG. 1.

As shown in FIG. 1, the blood glucose level of the mice in both the control group (CTL) and the experimental group (Os 50) before the treatment was about 360 mg/dL. After two weeks of treatment, the blood glucose level of the mice in the control group was elevated to 550 mg/dL, whereas the blood glucose level of the mice in the experimental group was maintained at about 360 mg/dL. The results prove that intraperitoneal administration of osthole can successfully control and lower the blood glucose level of db/db diabetic mice.

Example 2

Effect of Oral Administration of Osthole to Diabetic Mice

Six male db/db diabetic mice (5 to 7 week-old, purchased from National Laboratory Animal Center (Taipei, Taiwan)) were fasted for over 8 hours and venous blood was collected for the measurement of blood glucose level. The mice were divided into two groups (control group and experimental group) on the basis of their blood glucose level and body weight. The mice in the control group were fed with PBS by gastric tube. The mice in the experimental group were fed with osthole (50 mg/kg body weight) by gastric tube. The PBS and osthole were administered once daily, five days a week for three weeks. The mice were then fasted for about 16 hours before being sacrificed and blood samples were collected for the measurement of blood glucose level. The results of blood glucose level measurement are shown in FIG. 2.

As shown in FIG. 2, the blood glucose level of the mice in both the control group (CTL) and the experimental group (Os 50) before the treatment was about 200 mg/dL. After three weeks of treatment, the blood glucose level of the mice in the control group was elevated to 400 mg/dL; whereas, the blood glucose level of the mice in the experimental group was maintained at about 210 mg/dL. The results prove that oral administration of osthole can successfully control and lower the blood glucose level of db/db diabetic mice.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for the treatment of type II diabetes mellitus and/or its complications comprising administering a therapeutically effective amount of osthole or a pharmaceutically acceptable derivative thereof to a subject in need thereof, wherein osthole is chemically synthesized or purified at a purity of at least 95%.

2. The method according to claim 1, wherein the therapeutically effective amount is about 10 to about 200 mg/kg/day.

3. The method according to claim 1, wherein the therapeutically effective amount is about 50 mg/kg/day.

4. The method according to claim 1, wherein the osthole or pharmaceutically acceptable derivative thereof is administered to the subject parenterally or orally.

5. The method according to claim 1, wherein the subject is a mammal.

6. The method according to claim 5, wherein the mammal is a human.

7. The method according to claim 1, further comprising administering a second agent effective for the treatment of diabetes mellitus.

8. The method according to claim 1, wherein osthole or a pharmaceutically acceptable derivative thereof is obtained from *Cnidium* plant.

9. The method according to claim 1, wherein osthole or a pharmaceutically acceptable derivative thereof is obtained from *Cnidium monnieri* (L.) Cuss.

10. The method according to claim 1, wherein osthole or a pharmaceutically acceptable derivative thereof is obtained from *Cnidium* fruit.

* * * * *